United States Patent
Moser et al.

(10) Patent No.: US 12,221,445 B2
(45) Date of Patent: *Feb. 11, 2025

(54) CRYSTALLINE SALTS OF 5-METHYL-(6S)-TETRAHYDROFOLIC ACID AND AMINO ETHYL ESTERS

(71) Applicant: MERCK PATENT GMBH, Darmstadt (DE)

(72) Inventors: Rudolf Moser, Schaffhausen (CH); Viola Groehn, Dachsen (CH); Ruth Boehni Stamm, Stein Am Rhein (CH); Fritz Blatter, Reinach (CH); Martin Szelagiewicz, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 997 days.

This patent is subject to a terminal disclaimer.

(21) Appl. No.: 17/258,040

(22) PCT Filed: Jul. 2, 2019

(86) PCT No.: PCT/EP2019/067705
§ 371 (c)(1),
(2) Date: Jan. 5, 2021

(87) PCT Pub. No.: WO2020/007843
PCT Pub. Date: Jan. 9, 2020

(65) Prior Publication Data
US 2021/0277006 A1 Sep. 9, 2021

(30) Foreign Application Priority Data

Jul. 6, 2018 (EP) .................................... 18182284
Apr. 11, 2019 (EP) .................................... 19168723

(51) Int. Cl.
*C07D 475/04* (2006.01)
*A61K 45/06* (2006.01)
*C07C 229/36* (2006.01)

(52) U.S. Cl.
CPC ............ *C07D 475/04* (2013.01); *A61K 45/06* (2013.01); *C07C 229/36* (2013.01); *C07B 2200/13* (2013.01)

(58) Field of Classification Search
CPC .... C07D 475/04; A61K 45/06; C07C 229/36; C07B 2200/13
See application file for complete search history.

(56) References Cited

U.S. PATENT DOCUMENTS 5,194,611 A    3/1993   Marazza et al.
5,382,581 A    1/1995   Marazza et al.
(Continued)

FOREIGN PATENT DOCUMENTS

CN    104356134 A    2/2015
CN    103664945 B    1/2016
(Continued)

OTHER PUBLICATIONS

International Search Report PCT/EP2019/067705 dated Aug. 8, 2019 (pp. 1-4).
(Continued)

*Primary Examiner* — Andrew D Kosar
*Assistant Examiner* — John D McAnany
(74) *Attorney, Agent, or Firm* — Millen White Zelano & Branigan; Csaba Henter

(57) ABSTRACT

The present invention refers to a crystalline salt comprising 5-methyl-(6S)-tetrahydrofolic acid and an amino acid ethyl ester like L-phenylalanine ethyl ester or L-methionine ethyl ester, wherein the molar ratio of 5-methyl-(6S)-tetrahydrofolic acid to amino acid ethyl ester is from 1:0.3 to 1:3.0 (in (Continued)

mol/mol) and/or hydrates and/or solvates thereof as well as to a process of obtaining the same.

37 Claims, 5 Drawing Sheets

(56) References Cited

U.S. PATENT DOCUMENTS

| | | | |
|---|---|---|---|
| 6,441,168 B1 | 8/2002 | Müller et al. | |
| 11,925,644 B2* | 3/2024 | Moser | A61P 25/28 |
| 11,992,491 B2* | 5/2024 | Moser | A61K 31/519 |
| 2016/0207925 A1 | 7/2016 | Fracchia | |

FOREIGN PATENT DOCUMENTS

| | | |
|---|---|---|
| CN | 107304212 A | 10/2017 |
| EP | 0455013 B1 | 6/1995 |
| JP | S37-10698 B | 8/1962 |

OTHER PUBLICATIONS

Search report in corresponding Chinese Application No. 201980044245.5 dated Feb. 14, 2023 (pp. 1-8) and english translation thereof (pp. 1-10).
Notice of Reasons for Refusal in corresponding Japanese Patent Application No. 2021-500079 dated Jun. 27, 2023 (pp. 1-4).

* cited by examiner

CRYSTALLINE SALTS OF 5-METHYL-(6S)-TETRAHYDROFOLIC ACID AND AMINO ETHYL ESTERS

The present invention is directed to crystalline salts comprising 5-methyl-(6S)-tetrahydrofolic acid and an amino acid ethyl ester wherein the molar ratio of 5-methyl-(6S)-tetrahydrofolic acid to the amino acid ethyl ester is from 1:0.3 to 1:3.0 (in mol/mol) and/or hydrates and/or solvates thereof.

Tetrahydrofolates are predominantly used as the calcium salt of 5-formyltetrahydrofolic acid (leucovorin and levoleucovorin), as the calcium salt of 5-methyltetrahydrofolic acid (Metafolin®), or as the sulfate salt of 5,10-methylenetetrahydrofolic acid (Modufolin®). Most prominent fields of use are for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

The calcium salt of 5-methyl-(6S)-tetrahydrofolic acid is used in particular as a drug and as a food additive, as a vitamin preparation, for the prevention of neural tube defects, for the treatment of depressive illnesses, and for influencing the homocysteine level.

5-Methyl-(6S)-tetrahydrofolic acid and salts thereof are known to be extremely unstable. In particular they are highly susceptible to oxidation [see also A. L. Fitzhugh, Pteridines 4 (4), 187-191 (1993) in this respect] and therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid and salts thereof.

U.S. Pat. No. 6,441,168 B1 discloses alkaline earth metal salts of 5-methyltetrahydrofolic acid, particularly the calcium salt, its crystallization and its use. The drawback of such crystalline calcium salt of 5-methyl-(6S)-tetrahydrofolic acid is that it exists in its crystalline form in up to four polymorphic modifications. Therefore the process of manufacturing the crystalline calcium salt of 5-methyl-(6S)-tetrahydrofolic acid has to be controlled very precisely. Additionally the crystalline calcium salt of 5-methyl-(6S)-tetrahydrofolic acid of U.S. Pat. No. 6,441,168 B1 typically contains in the crystal lattice of all its polymorphic forms at least one but up to four equivalents of water per equivalent of 5-methyl-(6S)-tetrahydrofolic acid.

US 2016207925 A1 is claiming lyophilised, spray-dried or boiled down compositions comprising L-asparagine or L-arginine together with 5-methyl-(6S)-tetrahydrofolic acid. However the disclosed compositions are simple, non-stochiometric mixtures and exist in an amorphous state.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of tetrahydrofolates it is always the aim to provide a compound which has a low water absorption upon storage and which can be dried sufficiently during manufacturing. In addition, drug substances that do not absorb high amounts of water under ambient conditions are highly desired. Particularly desired are substances that do not change their water content when the ambient relative humidity changes because large changes of the water content due to change of the relative humidity of the environment make it more difficult to achieve a great precision with the respect to the dosage form.

The technical problem is solved by crystalline salts comprising 5-methyl-(6S)-tetrahydrofolic acid and an amino acid ethyl ester wherein the molar ratio of 5-methyl-(6S)-tetrahydrofolic acid to the amino acid ethyl ester is from 1:0.3 to 1:3.0 (in mol/mol) and/or hydrates and/or solvates thereof.

The solid form of the present invention possesses improved pharmacological characteristics, thus offering enhanced possibilities to modulate and design improved drug products.

Another advantageous aspect of the crystalline salt of 5-methyl-(6S)-tetrahydrofolic acid and an amino acid ethyl ester is that a high chemical and optical purity of 5-methyl-(6S)-tetrahydrofolic acid can be achieved in one single crystallization step.

It is advantageous when a drug has a high kinetic solubility when orally administered leading to an improved and faster bioavailability. Consequently, the medicament can function more readily.

5-methyl-(6S)-tetrahydrofolic acid is poorly soluble in water. The thermodynamically stable form of the calcium salt (Form III) exhibits an aqueous solubility of about 2.5 mg/ml and the solubility of the metastable Form I is about 10 mg/ml at room temperature. Under certain pH conditions, in particular when the pH of the environments is lower than the equilibrium pH of a given salt, the salts can potentially disproportionate into free acid and as a consequence, the solubility decreases substantially. Therefore, thermodynamic solubilities of the claimed salts at about neutral to lower pH values are inaccessible due to slow salt disproportionation (formation of poorly soluble free acid). However the bioavailability is dominated by kinetic effects. Administration of a solid form of a drug product is followed by dissolution and after the first dissolution step the drug is diluted by body fluids and distributed. Therefore the kinetic solubility is a key parameter that influences the bioavailability because the initially dissolved drug substance is readily diluted and transported. For the salt of 5-methyl-(6S)-tetrahydrofolic acid and an amino acid ethyl ester like L-phenylalanine ethyl ester it was surprisingly found that the kinetic solubility is improved by about 50% versus the known (metastable Form I) of the calcium salt. The difference in the kinetic solubility of the salt of the present invention to the thermodynamically stable form of the calcium salt (Form Ill) would presumably even be larger. Thus temporarily a much higher drug substance concentration can be achieved.

In a preferred embodiment, the amino acid ethyl ester is L-phenylalanine ethyl ester or L-methionine ethyl ester.

Preferably, the molar ratio of 5-methyl-(6S)-tetrahydrofolic acid to the amino acid ethyl ester is from 1:0.5 to 1:2.5 (in mol/mol).

Even more preferred, the molar ratio of 5-methyl-(6S)-tetrahydrofolic acid to the amino acid ethyl ester is from 1:0.75 to 1:1.25 (in mol/mol) and most preferred the molar ratio is approximately 1:1 (in mol/mol).

Alternatively, the molar ratio of 5-methyl-(6S)-tetrahydrofolic acid to the amino acid ethyl ester may be from 1:1.75 to 1:2.25 (in mol/mol) and/or hydrates and/or solvates thereof and most preferred the molar ratio is approximately 1:2 (in mol/mol).

Preferably, the amino acid ethyl ester is L-phenylalanine ethyl ester or L-methionine ethyl ester and the ratio of 5-methyl-(6S)-tetrahydrofolic acid to L-phenylalanine ethyl ester or L-methionine ethyl ester is approximately 1:2 (in mol/mol) and/or hydrates and/or solvates thereof.

More preferred, that the salt of the present invention is the crystalline salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 4.0, 6.4, 15.0, 15.9, 17.1, 18.4, 18.6, 21.9, 22.6, and 25.5 (Form A).

Most preferred, the salt of the present invention is the crystalline salt of 5-methyl-(6S)-tetrahydrofolic acid and L-phenylalanine ethyl ester and has a PXRD pattern with at least three characteristic peaks (expressed in 2θ±0.2° 2θ (CuKα radiation)) selected from the following peaks located at 4.0, 6.4, 15.0, 15.9, 17.1, 18.4, 18.6, 21.9, 22.6, and 25.5 (Form A) and even more preferred, that the salt of the present invention is the crystalline salt of 5-methyl-(6S)-tetrahydrofolic acid and L-phenylalanine ethyl ester and has a PXRD pattern with peaks (expressed in 2θ±0.2° 2θ (CuKα radiation)) at 4.0, 6.4, 15.0, 15.9, 17.1, 18.4, 18.6, 21.9, 22.6, and 25.5 (Form A).

Preferably, the salt of the present invention is the crystalline salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 4.0, 6.4, 7.3, 7.9, 12.5, 13.5, 13.9, 14.3, 15.0, 15.9, 17.1, 17.4, 17.9, 18.2, 18.4, 18.6, 20.1, 21.1, 21.9, 22.6, 24.3 and 25.5 (Form A) and most preferred, the salt of the present invention is the crystalline salt of 5-methyl-(6S)-tetrahydrofolic acid and L-phenylalanine ethyl ester and has a PXRD pattern substantially as shown in FIG. 1 (Form A).

Preferably, the salt of the present invention is the crystalline salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 3.7, 6.8, 7.5, 13.2, 14.9, 17.8 and 18.3 (Form B).

Most preferred, the salt of the present invention is the crystalline salt of 5-methyl-(6S)-tetrahydrofolic acid and L-phenylalanine ethyl ester and has a PXRD pattern with at least three characteristic peaks (expressed in 2θ±0.2° 2θ (CuKα radiation)) selected from the following peaks located at 3.7, 6.8, 7.5, 13.2, 14.9, 17.8 and 18.3 (Form B) and most preferred, the salt of the present invention is the crystalline salt of 5-methyl-(6S)-tetrahydrofolic acid and L-phenylalanine ethyl ester and has a PXRD pattern with peaks (expressed in 2θ±0.2° 2θ (CuKα radiation)) at 3.7, 6.8, 7.5, 13.2, 14.9, 17.8 and 18.3 (Form B).

Preferably, the salt of the present invention is the crystalline salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 3.7, 6.8, 7.5, 13.2, 14.9, 15.7, 16.2, 17.8, 18.3, 18.6, 19.0, 19.2, 19.5, 19.7, 21.3, 23.2, 23.6, 25.4 and 25.9 (Form B) and most preferred, the salt of the present invention is the crystalline salt of 5-methyl-(6S)-tetrahydrofolic acid and L-phenylalanine ethyl ester and has a PXRD pattern substantially as shown in FIG. 2 (Form B).

Further preferred, the salt of the present invention is the crystalline salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 5.5, 7.0, 8.5, 14.0, 14.7, and 17.7 (Form A).

More preferred, that the salt of the present invention is the crystalline salt of 5-methyl-(6S)-tetrahydrofolic acid and L-methionine ethyl ester and has a PXRD pattern with at least three characteristic peaks (expressed in 2θ±0.2° 2θ (CuKα radiation)) selected from the following peaks located at 5.5, 7.0, 8.5, 14.0, 14.7 and 17.7 (Form A) and even more preferred, that the salt of the present invention is the crystalline salt of 5-methyl-(6S)-tetrahydrofolic acid and L-methionine ethyl ester and has a PXRD pattern with peaks (expressed in 2θ±0.2° 2θ (CuKα radiation)) at 5.5, 7.0, 8.5, 14.0, 14.7, and 17.7 (Form A).

Preferably, the salt of the present invention is the crystalline salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 3.5, 5.5, 7.0, 8.5, 13.2, 14.0, 14.7, 17.7, 18.4, 21.6, 23.0, 23.9, and 27.6 (Form A) and most preferred, the salt of the present invention is the crystalline salt of 5-methyl-(6S)-tetrahydrofolic acid and L-methionine ethyl ester and has a PXRD pattern substantially as shown in FIG. 4 (Form A).

Further preferred, the salt of the present invention is the crystalline salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 7.3, 14.0, 14.7, 15.7, and 18.3 (Form B).

More preferred, that the salt of the present invention is the crystalline salt of 5-methyl-(6S)-tetrahydrofolic acid and L-methionine ethyl ester and has a PXRD pattern with at least three characteristic peaks (expressed in 2θ±0.2° 2θ (CuKα radiation)) selected from the following peaks located at 7.3, 14.0, 14.7, 15.7, and 18.3 (Form B) and even more preferred, that the salt of the present invention is the crystalline salt of 5-methyl-(6S)-tetrahydrofolic acid and L-methionine ethyl ester and has a PXRD pattern with peaks (expressed in 2θ±0.2° 2θ (CuKα radiation)) at 7.3, 14.0, 14.7, 15.7, and 18.3 (Form B).

Preferably, the salt of the present invention is the crystalline salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 5.0, 7.3, 8.5, 10.2, 13.8, 14.0, 14.7, 15.7, 18.3, 18.7, 20.5, 20.9, 22.2, 24.1, and 24.5 (Form B) and most preferred, the salt of the present invention is the crystalline salt of 5-methyl-(6S)-tetrahydrofolic acid and L-methionine ethyl ester and has a PXRD pattern substantially as shown in FIG. 5 (Form B).

Even more preferred, the aforementioned crystalline salts have at least 99 wt % or more chemical and/or stereoisomerical purity.

Comparing the salt of 5-methyl-(6S)-tetrahydrofolic acid and an amino acid ethyl ester with the calcium salt of 5-methyl-(6S)-tetrahydrofolic shows that the water content of the salt of 5-methyl-(6S)-tetrahydrofolic acid and an amino acid ethyl ester changes less. In addition to that the salt of 5-methyl-(6S)-tetrahydrofolic acid and an amino acid ethyl ester can easily be dried to a very low water content such as below 1%. So e.g. for the salt of 5-methyl-(6S)-tetrahydrofolic acid and L-phenylalanine ethyl ester the change in water content is less than 0.3% (Example 5, FIG. 3 solid line) within the most relevant range of range between 20% and 75% while the water content for the calcium salt of 5-methyl-(6S)-tetrahydrofolic acid changes by about 3% (Reference example 5, FIG. 3 dashed line).

It is advantageous having a salt comprising 5-methyl-(6S)-tetrahydrofolic with a very low water content and especially a low tendency to absorb/desorb water, e.g. when handling the substance for compounding in a temperature/humidity controlled environment or in tropical countries, where the relative humidity generally is very high.

The crystalline salt of 5-methyl-(6S)-tetrahydrofolic acid and L-methionine ethyl ester contains in its anhydrous form (Form A) typically below 1% of water at 50% to 60% relative humidity. The crystalline salt of 5-methyl-(6S)-tetrahydrofolic acid and L-methionine ethyl ester contains in its hydrated form (Form B) typically about 5% of water at 50 to 60% relative humidity, which as at the level of the calculated water content for a sesquihydrate which is 4.1%.

The significantly lower effect of humidity on the water adsorption of the crystalline salt of 5-methyl-(6S)-tetrahydrofolic acid and an amino acid ethyl ester like L-phenylalanine ethyl ester is leading to substantially improved control over the target dosage form level in the drug product because of the change of the amounts of adsorbed water under changing relative humidity conditions is significantly less pronounced.

This result is very surprising to a person skilled in the art and could not be expected when considering the teaching of U.S. Pat. No. 6,441,168 B1. Moreover, the salt of 5-methyl-(6S)-tetrahydrofolic acid and an amino acid ethyl ester of the present invention clearly solves the technical problem underlying the present invention.

Thus, the salt of the present invention exhibits improved storage stability even under these conditions. These improved properties were not derivable bearing the teaching of U.S. Pat. No. 6,441,168 B1 in mind.

Additionally the kinetic solubility of the crystalline salt of 5-methyl-(6S)-tetrahydrofolic acid and an amino acid ethyl ester like L-phenylalanine ethyl ester or L-methionine ethyl ester is higher compared with the calcium salt of 5-methyl-(6S)-tetrahydrofolic acid known in the art. According to Example 6 11.3 mg of the salt of 5-methyl-(6S)-tetrahydrofolic acid and L-phenylalanine ethyl ester dissolve within one minute in 2.00 ml water, whereas only 9.0 mg of 5-methyl-(6S)-tetrahydrofolic acid dissolve in the same amount of water when the calcium salt is used. The kinetic solubility of the crystalline salt of 5-methyl-(6S)-tetrahydrofolic acid and L-methionine ethyl ester at r.t is about 24 to 30 mg/ml of the salt which corresponds to a solubility which is greater than 18 mg/ml of 5-methyl-(6S)-tetrahydrofolic acid. This is considerably greater than the kinetic solubility of the calcium salt (which is lower than 10 mg/ml). Consequently, the salts of the present invention exhibit a better kinetic solubility when orally administered leading to an improved and faster bioavailability. Consequently, the medicament can function more readily.

A further aspect of the present invention is a process for obtaining the crystalline salt comprising 5-methyl-(6S)-tetrahydrofolic acid and an amino acid comprising the steps of:

i) providing a mixture of 5-methyl-(6S)-tetrahydrofolic acid and an amino acid ethyl ester, optionally in a suitable solvent or a mixture of solvents ii) adding a base, optionally in a suitable solvent or a mixture of solvents; iii) heating the composition to at least 60° C. and optionally carrying out a clear filtration;

iv) crystallizing and cooling the mixture to a temperature between 1° C. and 30° C., optionally adding more solvent or mixture of solvents; and v) isolating the obtained solid material and optionally drying the product.

Preferably, the molar ratio of 5-methyl-(6S)-tetrahydrofolic acid and the amino acid ethyl ester in step i) is in the range of from 1:1 to 1:3.

More preferred, the solvent is water.

In step iii) and/or iv) seed crystals may be added.

Preferably, the amino acid ethyl ester is L-phenylalanine ethyl ester or L-methionine ethyl ester. Even more preferred L-phenylalanine ethyl ester resp. L-methionine ethyl ester is added as L-phenylalanine ethyl ester hydrochloride resp. L-methionine ethyl ester hydrochloride.

Also, a pharmaceutical composition, food additive and/or preparation comprising the crystalline salt comprising 5-methyl-(6S)-tetrahydrofolic acid and an amino acid ethyl ester and optionally one or more acceptable excipients is part of the present invention.

Preferably, the amino acid ester is L-phenylalanine ethyl ester or L-methionine ethyl ester.

The pharmaceutical composition may be in the form of tablets, capsules, oral liquid preparations, powders, lyophilisates, granules, lozenges, reconstitutable powders, injectable or infusable solutions or suspensions or suppositories.

The pharmaceutical composition may further comprise at least one additional therapeutic agent and, preferably, is a pharmaceutical composition for oral, parenteral, intramuscular, intraspinal, intrathecal, peridontal, topical or rectal administration.

The use of the crystalline salt comprising 5-methyl-(6S)-tetrahydrofolic acid and an amino acid ethyl ester as constituent for the production of drugs and/or as a food additive is also covered by the present invention. Preferably, the amino acid ethyl ester is L-phenylalanine ethyl ester or L-methionine ethyl ester.

The crystalline salt comprising 5-methyl-(6S)-tetrahydrofolic acid and an amino acid ethyl ester can be used in the treatment in homocysteine-lowering, of anemia, neural tube defects, cardiovascular diseases, depression, cognitive impairment, Alzheimer's disease and osteoporosis and/or dietary management of low plasma and/or low red blood cell and/or low cerebrospinal fluid and/or low peripheral or central nervous system folate. Preferably, the amino acid ethyl ester is L-phenylalanine ethyl ester or L-methionine ethyl ester.

In summary, the profile of properties offered by the salt of 5-methyl-(6S)-tetrahydrofolic acid and an amino acid ethyl ester like L-phenylalanine ethyl ester or L-methionine ethyl ester of the present invention is advantageous for use in medicaments or as food additive. Especially, the low change in water content in an environment from 20% to 75% relative humidity could not been foreseen by the skilled artisan.

Moreover, the kinetic solubility is higher, what could also not be foreseen by the skilled artisan.

EXAMPLES

Powder X-Ray Diffraction

Figure 1:
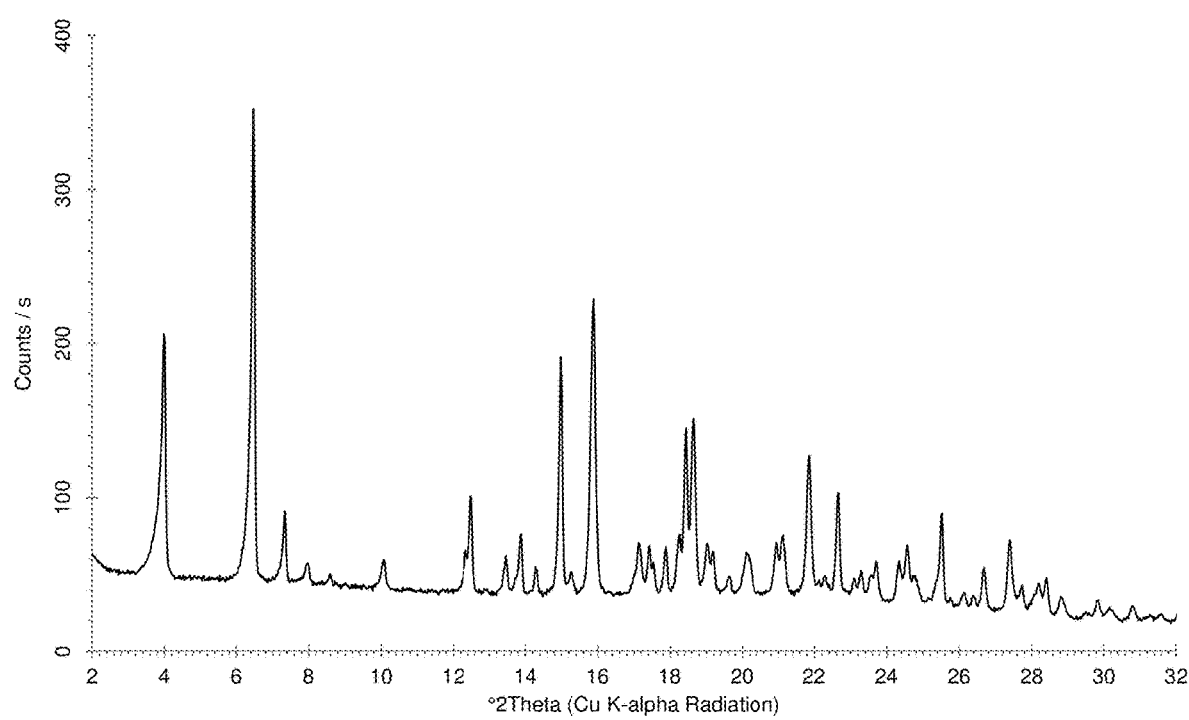
FIG. 1 Powder X-ray diffraction pattern of the crystalline salt comprising 5-methyl-(6S)-tetrahydrofolic acid salt and L-phenylalanine ethyl ester 1:2 (Form A).

Stoe Stadi P equipped with a Mythen1 K Detector; Cu-Kα1 radiation; standard measurement conditions: transmission; 40 kV and 40 mA tube power; curved Ge monochromator; 0.02°2θ step size, 48 s step time, 1.5-50.5°2θ scanning range; detector mode: step scan; 1°2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed with an SPS11-100n "Sorptions Prufsystem" from ProUmid (formerly "Projekt Messtechnik"), August-Nagel-Str. 23, 89079 Ulm (Germany).

Raman Spectroscopy

FT-Raman spectra were recorded on a Bruker MultiRAM FT-Raman or a Bruker RFS 100 FT-Raman system with a near infrared Nd:YAG laser operating at 1064 nm and a liquid nitrogen-cooled germanium detector. 64 scans with a resolution of 2 $cm^{-1}$ were accumulated in the range from 3500 to −50 $cm^{-1}$; however, only data above 100 $cm^{-1}$ are evaluated due to filter cutoff effects. Nominal laser powers are typically 100 or 300 mW.

Example 1: Preparation of a Crystalline Salt of 5-methyl-(6S)-tetrahydrofolic Acid and L-Phenylalanine Ethyl Ester with Heteroseeding To a mixture of 15 g of L-phenylalanine ethyl ester hydrochloride and 100 mL acetic acid ethylester in a separating funnel was added 200 mL of a saturated aqueous solution of sodium hydrogen carbonate. After mixing the acetic acid ethylester layer was separated form the aqueous layer. The acetic acid ethylester layer was combined with the extracts that were obtained from washing the aqueous layer three times with in each case 100 mL of acetic acid ethylester. The combined layers were washed with 50 mL of an aqueous saturated solution of sodium chloride, dried over magnesium chloride to give 12.44 g of an oily residue after evaporation of acetic acid ethyl ester in vacuum at 40° C. 9.87 g of the oily residue were added dropwise within approximately 10 min. to a mixture of 10 g of 5-methyl-(6S)-tetrahydrofolic acid and 30 mL of water in a glass vessel at 75-80° C. while stirring under a nitrogen atmosphere. The mixture was stirred for approximately 2 hours at about 80° C. and then cooled to about 20° C. within about 3 hours. Some drops of the solution in the glass vessel were applied to a glass plate and diluted with some drops of ethanol and 1 molar aqueous hydrochloric acid. After addition of a small amount of crystalline dibenzylamine salt of 5-methyl-(6S)-tetrahydrofolic acid (prepared according to EP EP0455013) for heteroseeding and storage of the glass plate at ambient temperature over night without coverage, yellow crystals were formed.

The mixture in the glass vessel was stirred for approximately 15 hours at ambient temperature and then cooled within about 105 minutes to about 2° C. and stirred for approximately 1 hour at about 2° C. Then the crystals that were formed on the glass plate were added to the glass vessel. The glass vessel was scratched with a glass rod which results in formation of a thick off white suspension within about 3 hours at about 2° C. The solid product was isolated by filtration (suction) and washed with 50 mL of water that was pre-cooled in an ice-bath. The product was dried for about 60 hours at ambient temperature in vacuum (10 mbar) to give 13.6 g of a white crystalline solid. By $^1$H-NMR spectroscopy a ratio of 1:1.8 of 5-methyl-(6S)-tetrahydrofolic acid to L-phenylalanine ethyl ester was determined.

Example 2: Preparation of a Crystalline Salt of 5-methyl-(6S)-tetrahydrofolic Acid and L-phenylalanine Ethyl Ester with Seeding All operations were performed under nitrogen atmosphere. To a mixture of 3.00 grams of 5-methyl-(6S)-tetrahydrofolic acid ([6S]-content 98.4%) and 20 ml of water a solution of 4.49 grams of L-phenylalanine ethyl ester hydrochloride in 20 mL of water were added at room temperature while stirring. The suspension was heated to about 77° C. and by addition of 1.3 mL of an aqueous solution of sodium hydroxide (assay sodium hydroxide 32% w/w) a clear solution was obtained. The heating bath was removed to allow the solution to cool to about 27° C. within about one hour. While cooling, the solution was seeded at about 72° C. and at about 27° C. with small amounts of crystalline salt of 5-methyl-(6S)-tetrahydrofolic acid and L-phenylalanine ethyl ester and gradually changed into a concentrated suspension. The thick suspension was stirred at ambient temperature for about 20 hours. The solid product was isolated by filtration using a fritted glass filter and washed twice with ten mL of cold water each time. The solids were dried in a vacuum dryer at about 40° C./10 mbar and examined by $^1$H-NMR and identified as 5-methyl-(6S)-tetrahydrofolic acid L-phenylalanine ethyl ester 1:2 salt. Powder X-ray diffraction was carried out and a PXRD pattern of the L-phenylalanine ethyl ester salt Form A, substantially as depicted in FIG. 1 was obtained. According to PXRD the sample contained a small amount of NaCl.

HPLC analysis showed that the purity was 98.9% area and the optical purity was increased to 99.6% [6S]-diastereoisomer.

Figure 2:
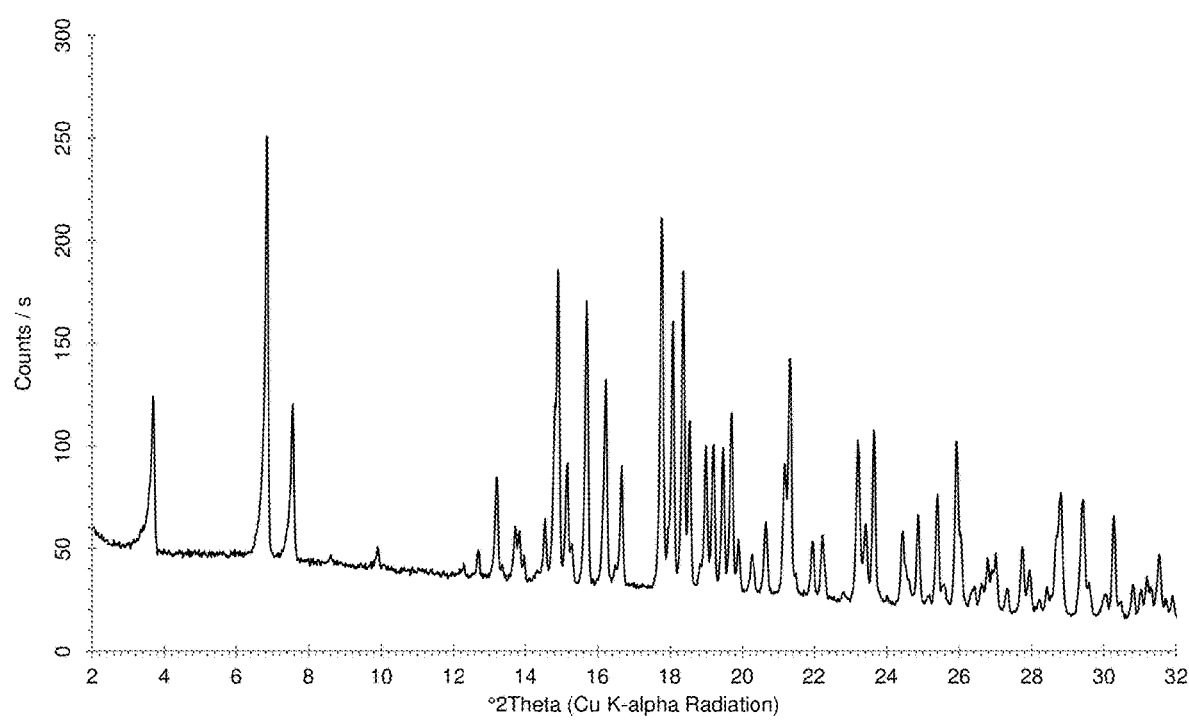
FIG. 2 Powder X-ray diffraction pattern of the crystalline salt comprising 5-methyl-(6S)-tetrahydrofolic acid salt and L-phenylalanine ethyl ester 1:2 (Form B).

Example 3: Washing the Salt of 5-methyl-(6S)-tetrahydrofolic Acid and L-phenylalanine Ethyl Ester 0.41 grams of the solid material obtained in Example 2 was weighed into a filter centrifuge device and 2.0 mL of water were added followed by centrifugation under ambient conditions. This wash step was repeated twice more using 0.5 mL of water. The wet filter cake was then transferred into a fritted glass filter and air dried by drawing ambient air (about 22° C./about 22% r.h.) through the glass filter for about 10 30 minutes. The dried material was examined by $^1$H-NMR and identified as a 5-methyl-(6S)-tetrahydrofolic acid L-phenylalanine ethyl ester 1:2 salt. Analysis of the sample by TG-FTIR showed a water content of about 5.9% (w/w). An aliquot of the sample was prepared between two acetate foils for PXRD at room temperature at about 25% relative humidity. Powder X-ray diffraction was carried out and a PXRD pattern of the L-phenylalanine ethyl ester salt Form B was obtained. No NaCl was detected in the PXRD pattern of the L-phenylalanine ethyl ester salt Form B which is depicted in FIG. 2 and exhibits peaks at 2-theta angles as listed in Table 1.

Table 1: 2-theta angles, d-spacings and qualitative intensities for the salt of 5-methyl-(6S)-tetrahydrofolic acid and L-phenylalanine ethyl ester Form B according to Example 3. Vs=very strong, s=strong, m=medium, w=weak, and vw=very weak in intensity. It should be noted that intensity values can vary substantially due to preferred orientation effects.

| angle °2θ | d-spacing [Å] | qualitative intensity |
|---|---|---|
| 3.7 | 24.1 | s |
| 6.8 | 12.9 | vs |
| 7.5 | 11.7 | s |
| 8.6 | 10.3 | m |
| 9.9 | 8.9 | m |
| 12.3 | 7.2 | m |
| 12.7 | 7.0 | m |
| 13.2 | 6.7 | s |
| 13.8 | 6.4 | m |
| 14.5 | 6.1 | m |
| 14.9 | 5.95 | vs |
| 15.1 | 5.85 | s |
| 15.7 | 5.64 | s |
| 16.2 | 5.46 | s |
| 16.7 | 5.32 | s |
| 17.8 | 4.99 | vs |
| 18.1 | 4.91 | s |
| 18.3 | 4.83 | vs |
| 18.6 | 4.78 | s |
| 19.0 | 4.67 | s |
| 19.2 | 4.62 | s |
| 19.5 | 4.56 | s |
| 19.7 | 4.50 | s |
| 19.9 | 4.45 | m |
| 20.3 | 4.38 | m |
| 20.6 | 4.30 | m |
| 21.3 | 4.17 | s |
| 21.9 | 4.05 | m |
| 22.2 | 3.99 | m |
| 22.8 | 3.90 | w |
| 23.2 | 3.83 | s |
| 23.6 | 3.76 | s |
| 24.5 | 3.64 | m |
| 24.9 | 3.58 | m |
| 25.4 | 3.50 | s |
| 25.9 | 3.43 | s |
| 26.4 | 3.38 | w |
| 26.8 | 3.32 | m |
| 27.0 | 3.30 | m |
| 27.3 | 3.26 | w |
| 27.7 | 3.21 | m |
| 27.9 | 3.19 | m |
| 28.2 | 3.16 | w |
| 28.4 | 3.14 | w |
| 28.8 | 3.10 | s |
| 29.4 | 3.03 | m |
| 30.0 | 2.97 | w |
| 30.3 | 2.95 | m |
| 30.8 | 2.90 | w |
| 31.2 | 2.86 | w |
| 31.5 | 2.84 | m |
| 31.9 | 2.80 | w |
| 32.2 | 2.78 | m |

Example 4: Vacuum Drying of the Salt of 5-methyl-(6S)-tetrahydrofolic Acid and L-phenylalanine Ethyl Ester About 100 mg of the crystalline material according to Example 3 were vacuum dried at about 50° C. and about 10 mbar for about two hours. When the sample was recovered from the vacuum dryer the ambient temperature was about 23° C. and the relative humidity was 24%. Analysis of the sample by TG-FTIR showed a water content of about 2.5% w/w. An aliquot of the sample was prepared between two acetate foils for PXRD at room temperature and about 25% relative humidity. Powder X-ray diffraction was carried out and a PXRD pattern of the L-phenylalanine ethyl ester salt Form A was obtained. No NaCl was detected in the PXRD pattern. The powder X-ray diffraction pattern of the L-phenylalanine ethyl ester salt Form A is depicted in FIG. 1 and exhibits peaks at 2-theta angles as listed in Table 2.

Table 2: 2-theta angles, d-spacings and qualitative intensities for the salt of 5-methyl-(6S)-tetrahydrofolic acid and L-phenylalanine ethyl ester Form A according to Example 3. Vs=very strong, s=strong, m=medium, w=weak, and vw=very weak in intensity. It should be noted that intensity values can vary substantially due to preferred orientation effects.

| angle °2θ | d-spacing [Å] | qualitative intensity |
|---|---|---|
| 4.0 | 22.3 | s |
| 6.4 | 13.7 | vs |
| 7.3 | 12.1 | m |
| 7.9 | 11.1 | m |
| 8.6 | 10.3 | w |
| 10.1 | 8.8 | m |
| 12.5 | 7.1 | m |
| 12.9 | 6.8 | w |
| 13.5 | 6.6 | m |
| 13.9 | 6.4 | m |
| 14.3 | 6.2 | m |
| 15.0 | 5.92 | s |
| 15.3 | 5.80 | w |
| 15.9 | 5.58 | s |
| 17.1 | 5.17 | m |
| 17.4 | 5.08 | m |
| 17.9 | 4.96 | m |
| 18.2 | 4.87 | m |

| angle °2θ | d-spacing [Å] | qualitative intensity |
|---|---|---|
| 18.4 | 4.81 | s |
| 18.6 | 4.76 | s |
| 19.0 | 4.66 | m |
| 19.6 | 4.52 | w |
| 20.1 | 4.41 | m |
| 21.1 | 4.20 | m |
| 21.9 | 4.06 | s |
| 22.3 | 3.99 | w |
| 22.6 | 3.92 | m |
| 23.1 | 3.85 | w |
| 23.3 | 3.82 | w |
| 23.7 | 3.75 | m |
| 24.3 | 3.65 | m |
| 24.5 | 3.62 | m |
| 24.8 | 3.59 | w |
| 25.5 | 3.49 | m |
| 26.1 | 3.41 | w |
| 26.4 | 3.37 | w |
| 26.7 | 3.34 | m |
| 27.4 | 3.25 | m |
| 27.7 | 3.22 | w |
| 28.2 | 3.16 | w |

Example 5: Dynamic Water Vapor Sorption Experiment with the Salt of 5-methyl-(6S)-tetrahydrofolic Acid and L-phenylalanine Ethyl Ester Form B 22 mg of the salt of 5-methyl-(6S)-tetrahydrofolic acid with L-phenylalanine ethyl ester Form B according to Example 2 was weighed into an aluminum sample pan for DVS measurement. A DVS measurement was performed. For relative humidity (RH) scans, change rates of 5% per hour were used. The sample pan was placed into the instrument and a defined relative humidity change program was started according to the following steps:
(1) Maintained RH for 2 hours at 50%, then
(2) scanned RH from 50→20% at a rate of 5% per hour and maintained RH at 20% for 10 hours, then
(3) scanned RH from 20→75% at a rate of 5% per hour and maintained RH at 75% for 10 hours, then
(4) scanned RH from 75→50% RH at a rate of 5% per hour and maintained RH at 50% for two hours.

Figure 3:
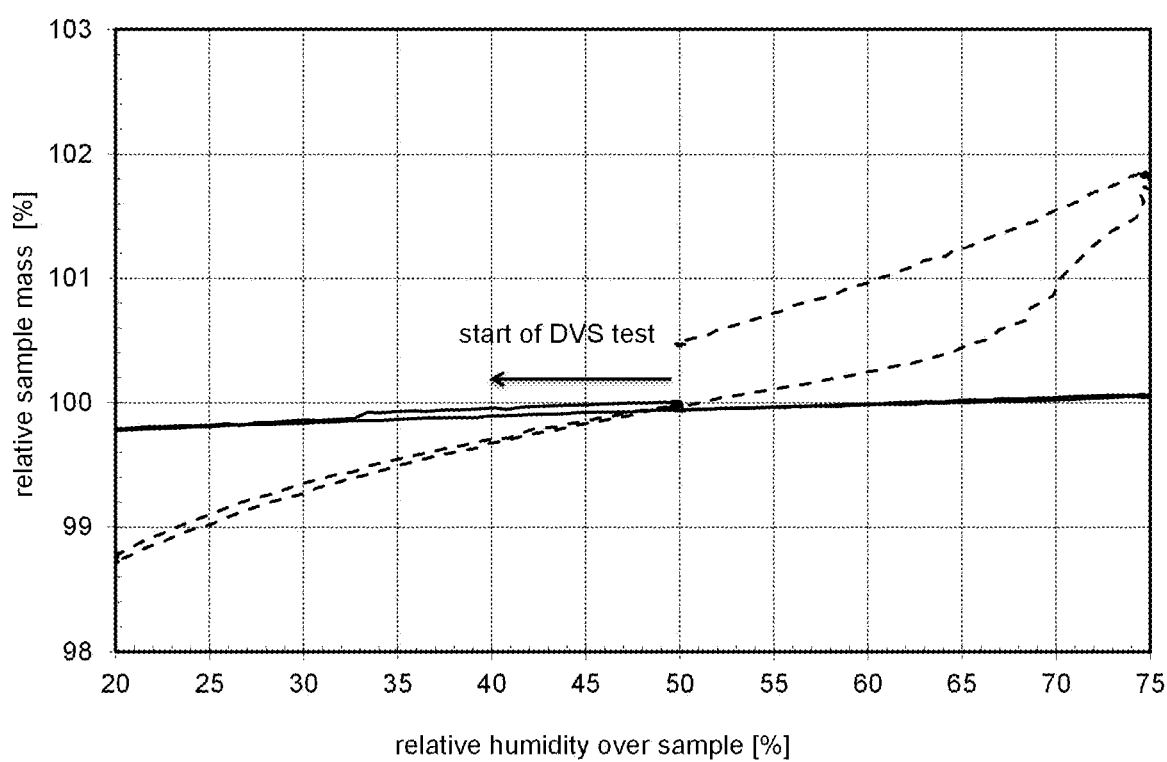
FIG. 3 DVS measurement of the salt of 5-methyl-(6S)-tetrahydrofolic acid with L-phenylalanine ethyl ester (solid line) and the calcium salt (dashed line).

In parallel, the very same protocol was applied to a sample of the calcium salt of 5-methyl-(6S)-tetrahydrofolic acid as a reference and the result for both is displayed in FIG. 3. During the test, the relative sample mass for the salt of 5-methyl-(6S)-tetrahydrofolic acid and L-phenylalanine ethyl ester (solid line) changed less than 0.3% while for the calcium salt (dashed line) the relative sample mass changed by about 3%.

Example 6: Kinetic Solubility of the Crystalline Salt of 5-methyl-(6S)-tetrahydrofolic Acid and L-phenylalanine Ethyl Ester 42.3 mg of the anhydrous form of the crystalline salt of 5-methyl-(6S)-tetrahydrofolic acid and L-phenylalanine ethyl ester according to Example 4 was weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute.

After one minute a turbid solution was observed suggesting that most of the sample was dissolved. The solution was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 11.3 mg of 5-methyl-(6S)-tetrahydrofolic acid per mL.

Example 7: Preparation of a Crystalline Salt of 5-methyl-(6S)-tetrahydrofolic Acid and L-methionine Ethyl Ester, Anhydrous Form (Form A)

15 g 5-methyl-(6S)-tetrahydrofolic acid (assay: 96.2% w/w, 6S-diastereoisomer: 98.1%) were added to 100 g water under a nitrogen atmosphere. After addition of 16.8 g L-methionine ethylester hydrochloride and 30 g water, the pH was adjusted to pH=7.0 by addition of aqueous sodium hydroxide (30% w/w), while keeping the temperature below 25° C. by cooling in an ice bath. The resulting solution was heated to 66° C. and the pH was adjusted to 5.4 by addition of aqueous 1 molar hydrochloric acid. The mixture was seeded with 5-methyl-(6S)-tetrahydrofolic acid L-isoleucine ethyl ester salt and cooled to 20° C. while maintaining the pH at 5.4 by addition of 1 molar hydrochloric acid. The crystallized product was isolated by suction and washed with 44 g water, that was pre cooled to 1° C. The material was dried at 20° C. in vacuum for 64 hours to give 14.9 g of 5-methyl-(6S)-tetrahydrofolic acid L-methionine ethyl ester salt corresponding to 74% of theoretical yield (assay corrected). The isolated product showed a purity of 98.6% area, an assay of 71.9% w/w 5-methyl-(6S)-tetrahydrofolic acid corresponding to the 1:1 salt, 1.2% w/w, and a 6S-diastereoisomeric purity of 99.9%.

Table 3: 2-theta angles, d-spacings and qualitative intensities for the salt of 5-methyl-(6S)-tetrahydrofolic acid and L-methionine ethyl ester anhydrous form (Form A) according to Example 7. Vs=very strong, s=strong, m=medium, w=weak, and vw=very weak in intensity. It should be noted that intensity values can vary substantially due to preferred orientation effects.

| angle °2θ | d-spacing [Å] | qualitative intensity |
|---|---|---|
| 3.5 | 25.4 | s |
| 4.2 | 20.8 | m |
| 5.1 | 17.3 | m |
| 5.5 | 16.0 | s |
| 7.0 | 12.7 | vs |
| 8.5 | 10.4 | s |
| 9.0 | 9.8 | m |
| 10.2 | 8.7 | m |
| 10.5 | 8.4 | m |
| 11.0 | 8.0 | m |
| 12.6 | 7.0 | m |
| 12.8 | 6.9 | m |
| 13.2 | 6.7 | s |
| 13.5 | 6.6 | m |
| 14.0 | 6.3 | vs |
| 14.7 | 6.00 | vs |
| 15.3 | 5.79 | s |
| 16.0 | 5.53 | s |
| 16.5 | 5.36 | m |
| 17.0 | 5.21 | s |
| 17.7 | 5.02 | vs |
| 17.9 | 4.95 | m |
| 18.4 | 4.81 | s |

-continued

| angle °2θ | d-spacing [Å] | qualitative intensity |
|---|---|---|
| 18.9 | 4.68 | s |
| 19.5 | 4.54 | s |
| 19.9 | 4.47 | m |
| 20.1 | 4.41 | m |
| 20.5 | 4.33 | m |
| 20.9 | 4.25 | m |
| 21.1 | 4.21 | s |
| 21.6 | 4.11 | vs |
| 22.3 | 3.99 | m |
| 22.5 | 3.94 | s |
| 23.0 | 3.86 | s |
| 23.4 | 3.80 | m |
| 23.9 | 3.73 | s |
| 24.3 | 3.65 | s |
| 24.9 | 3.57 | s |
| 25.4 | 3.50 | m |
| 25.5 | 3.49 | m |
| 25.7 | 3.46 | m |
| 26.1 | 3.42 | m |
| 26.4 | 3.37 | m |
| 26.8 | 3.32 | m |
| 27.3 | 3.27 | w |
| 27.6 | 3.23 | s |
| 28.1 | 3.18 | m |
| 28.4 | 3.14 | m |
| 28.8 | 3.10 | m |
| 29.2 | 3.05 | w |
| 29.6 | 3.01 | w |
| 29.8 | 2.99 | m |
| 32.0 | 2.80 | m |

Example 8: Preparation of a Crystalline Salt of 5-methyl-(6S)-tetrahydrofolic Acid and L-methionine Ethyl Ester, Hydrated Form (Form B)

A sample prepared according to Example 7 was treated according to the DVS measurement as disclosed in Example 5. Crystalline 5-methyl-(6S)-tetrahydrofolic acid salt and L-methionine ethyl ester, hydrated form (Form B) was obtained.

Figure 5:
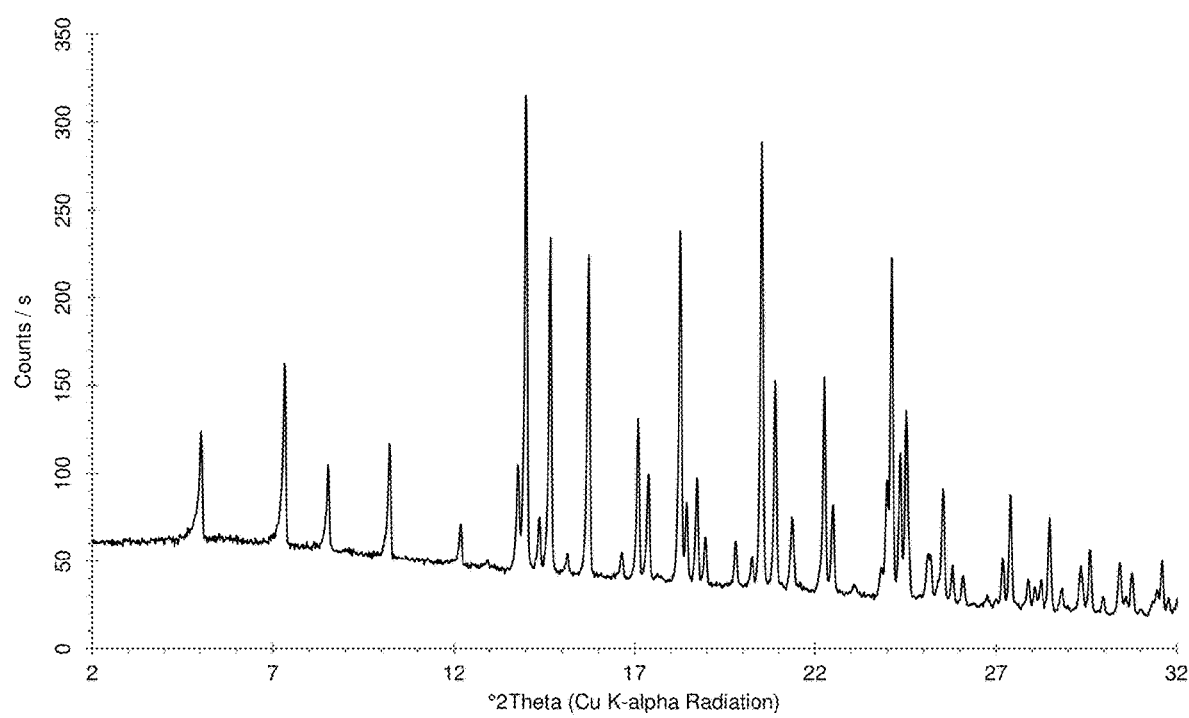
FIG. 5 Powder X-ray diffraction pattern of the crystalline salt comprising 5-methyl-(6S)-tetrahydrofolic acid salt and L-methionine ethyl ester, hydrated form (Form B).

The powder X-ray diffraction pattern of the L-methionine ethyl ester, hydrated form (Form B) is depicted in FIG. 5 and exhibits peaks at 2-theta angles as listed in Table 4.

Table 4: 2-theta angles, d-spacings and qualitative intensities for the salt of 5-methyl-(6S)-tetrahydrofolic acid and L-methionine ethyl ester hydrated form (Form B) according to Example 8. Vs=very strong, s=strong, m=medium, w=weak, and vw=very weak in intensity. It should be noted that intensity values can vary substantially due to preferred orientation effects.

| angle °2θ | d-spacing [Å] | qualitative intensity |
|---|---|---|
| 5.0 | 17.7 | s |
| 7.3 | 12.1 | s |
| 8.5 | 10.4 | s |
| 10.2 | 8.7 | s |
| 12.2 | 7.3 | m |
| 12.9 | 6.8 | m |
| 13.8 | 6.4 | s |
| 14.0 | 6.3 | vs |
| 14.4 | 6.2 | m |
| 14.7 | 6.0 | vs |
| 15.1 | 5.85 | m |
| 15.7 | 5.63 | vs |
| 16.6 | 5.32 | m |
| 17.1 | 5.19 | s |

-continued

| angle °2θ | d-spacing [Å] | qualitative intensity |
|---|---|---|
| 17.4 | 5.10 | s |
| 18.3 | 4.86 | vs |
| 18.5 | 4.79 | m |
| 18.7 | 4.74 | s |
| 18.9 | 4.68 | m |
| 19.8 | 4.48 | m |
| 20.2 | 4.39 | m |
| 20.5 | 4.33 | vs |
| 20.9 | 4.25 | s |
| 21.4 | 4.15 | m |
| 22.2 | 3.99 | s |
| 22.5 | 3.95 | m |
| 23.1 | 3.85 | w |
| 24.1 | 3.69 | vs |
| 24.5 | 3.63 | s |
| 25.2 | 3.54 | m |
| 25.5 | 3.49 | m |
| 25.8 | 3.45 | m |
| 26.1 | 3.41 | w |
| 26.7 | 3.33 | w |
| 27.2 | 3.28 | m |
| 27.4 | 3.25 | m |
| 27.9 | 3.20 | w |
| 28.2 | 3.16 | w |
| 28.5 | 3.13 | m |
| 29.6 | 3.01 | m |
| 30.4 | 2.94 | m |
| 31.6 | 2.83 | m |

Reference Example 1: Kinetic Solubility of the Calcium Salt of 5-methyl-(6S)-tetrahydrofolic Acid 42.5 mg of the anhydrous form of the crystalline 5-methyl-(6S)-tetrahydrofolic acid calcium salt was weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute. After one minute a suspension was observed. The suspension was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 9.0 mg of 5-methyl-(6S)-tetrahydrofolic acid per mL.

The invention claimed is:

1. A crystalline salt comprising 5-methyl-(6S)-tetrahydrofolic acid and an amino acid ethyl ester wherein the molar ratio of 5-methyl-(6S)-tetrahydrofolic acid to amino acid ethyl ester is from 1:0.3 to 1:3.0 (in mol/mol) and/or hydrates and/or solvates thereof.

2. The crystalline salt of claim 1, wherein the molar ratio of 5-methyl-(6S)-tetrahydrofolic acid to the amino acid ethyl ester is from 1:0.5 to 1:2.5 (in mol/mol) and/or hydrates and/or solvates thereof.

3. The crystalline salt of claim 1, wherein the molar ratio of 5-methyl-(6S)-tetrahydrofolic acid to the amino acid ethyl ester is from 1:0.75 to 1:2.25 (in mol/mol) and/or hydrates and/or solvates thereof.

4. The crystalline salt of claim 1, wherein the ratio of 5-methyl-(6S)-tetrahydrofolic acid to the amino acid ethyl ester is approximately 1:1 (in mol/mol) and/or hydrates and/or solvates thereof.

5. The crystalline salt of claim 1, wherein the ratio of 5-methyl-(6S)-tetrahydrofolic acid to the amino acid ethyl ester is approximately 1:2 (in mol/mol) and/or hydrates and/or solvates thereof.

6. The crystalline salt of claim 1, wherein the amino acid ethyl ester is L-phenylalanine ethyl ester and the molar ratio of 5-methyl-(6S)-tetrahydrofolic acid to L-phenylalanine ethyl ester is from 1:1.75 to 1:2.25 (in mol/mol) and/or hydrates and/or solvates thereof.

7. The crystalline salt of claim 1, wherein the amino acid ethyl ester is L-phenylalanine ethyl ester and the molar ratio of 5-methyl-(6S)-tetrahydrofolic acid to L-phenylalanine ethyl ester is approximately 1:2 (in mol/mol) and/or hydrates and/or solvates thereof.

8. The crystalline salt of claim 1, wherein the salt is the salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 4.0, 6.4, 15.0, 15.9, 17.1, 18.4, 18.6, 21.9, 22.6, and 25.5.

9. The crystalline salt of claim 1, wherein the salt is the salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 4.0, 6.4, 7.3, 7.9, 12.5, 13.5, 13.9, 14.3, 15.0, 15.9, 17.1, 17.4, 17.9, 18.2, 18.4, 18.6, 20.1, 21.1, 21.9, 22.6, 24.3 and 25.5.

10. The crystalline salt of claim 1, wherein the salt is the salt of 5-methyl-(6S)-tetrahydrofolic acid and L-phenylalanine ethyl ester and has a PXRD pattern as shown in FIG. 1 (Form A).

11. The crystalline salt of claim 1, wherein the salt is the salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 3.7, 6.8, 7.5, 13.2, 14.9, 17.8 and 18.3.

12. The crystalline salt of claim 1, wherein the salt is the salt of 5-methyl-(6S)-tetrahydrofolic acid and L-phenylalanine ethyl ester and has a PXRD pattern with at least one characteristic peak (expressed in 2θ±0.2° 2θ (CuKα radiation)) selected from the following peaks located at 3.7, 6.8, 7.5, 13.2, 14.9, 15.7, 16.2, 17.8, 18.3, 18.6, 19.0, 19.2, 19.5, 19.7, 21.3, 23.2, 23.6, 25.4 and 25.9.

13. The crystalline salt of claim 1, wherein the salt is the salt of 5-methyl-(6S)-tetrahydrofolic acid and L-phenylalanine ethyl ester and has a PXRD pattern as shown in FIG. 2 (Form B).

14. The crystalline salt of claim 1, wherein the amino acid ethyl ester is L-methionine ethyl ester and the molar ratio of 5-methyl-(6S)-tetrahydrofolic acid to L-methionine ethyl ester is from 1:0.75 to 1:1.25 (in mol/mol) and/or hydrates and/or solvates thereof.

15. The crystalline salt of claim 1, wherein the amino acid ethyl ester is L-methionine ethyl ester and the molar ratio of 5-methyl-(6S)-tetrahydrofolic acid to L-methionine ethyl ester is approximately 1:1 (in mol/mol) and/or hydrates and/or solvates thereof.

16. The crystalline salt of claim 1, wherein the salt is the salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 5.5, 7.0, 8.5, 14.0, 14.7, and 17.7.

17. The crystalline salt of claim 1, wherein the salt is the salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 3.5, 5.5, 7.0, 8.5, 13.2, 14.0, 14.7, 17.7, 18.4, 21.6, 23.0, 23.9, and 27.6.

Figure 4:
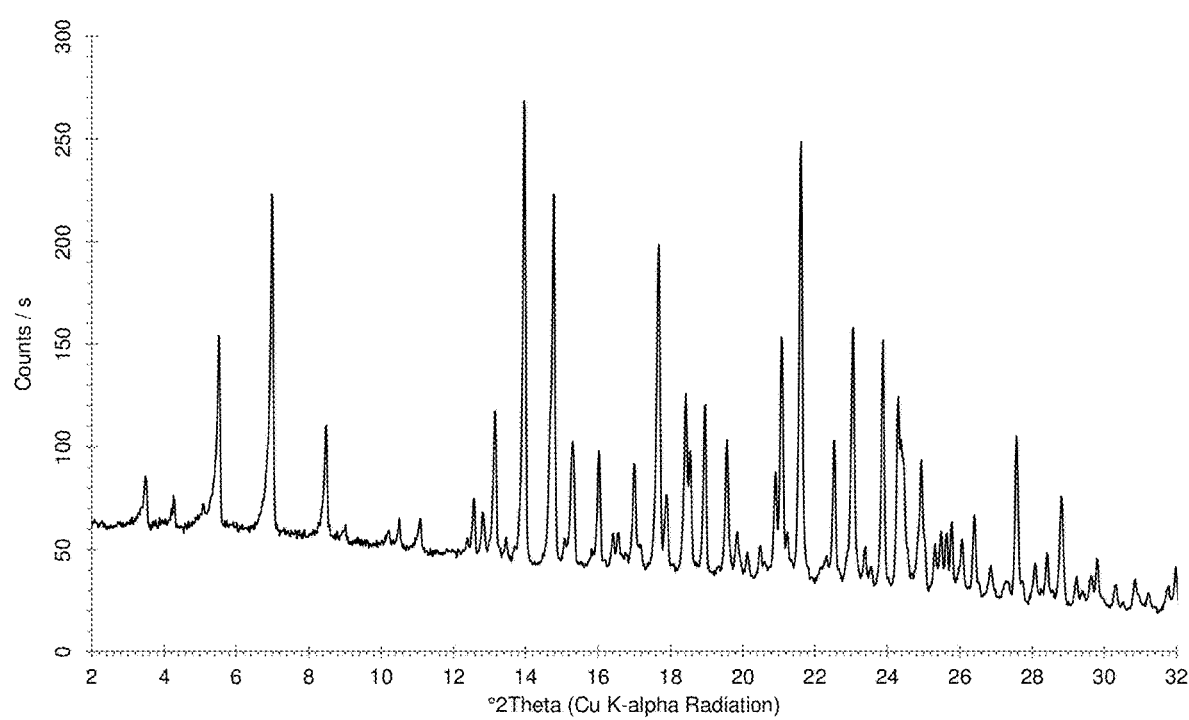
FIG. 4 Powder X-ray diffraction pattern of the crystalline salt comprising 5-methyl-(6S)-tetrahydrofolic acid salt and L-methionine ethyl ester, anhydrous form (Form. A).

18. The crystalline salt of claim 1, wherein the salt is the salt of 5-methyl-(6S)-tetrahydrofolic acid and L-methionine ethyl ester and has a B PXRD pattern as shown in FIG. 4 (Form A).

19. The crystalline salt of claim 1, wherein the salt is the salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 7.3, 14.0, 14.7, 15.7, and 18.3.

20. The crystalline salt of claim 1, wherein the salt is the salt of 5-methyl-(6S)-tetrahydrofolic acid and L-methionine ethyl ester and has a PXRD pattern with at least one characteristic peak (expressed in 2θ±0.2° 2θ (CuKα radiation)) selected from the following peaks located at 5.0, 7.3, 8.5, 10.2, 13.8, 14.0, 14.7, 15.7, 18.3, 18.7, 20.5, 20.9, 22.2, 24.1, and 24.5.

21. The crystalline salt of claim 1, wherein the salt is the salt of 5-methyl-(6S)-tetrahydrofolic acid and L-methionine ethyl ester and has a B PXRD pattern as shown in FIG. 5 (Form B).

22. A process for obtaining the crystalline salt comprising 5-methyl-(6S)-tetrahydrofolic acid and an amino acid ethyl ester according to claim 1 comprising the steps of:
  i) providing a mixture of 5-methyl-(6S)-tetrahydrofolic acid and an amino acid ethyl ester, optionally in a suitable solvent or a mixture of solvents
  ii) adding a base, optionally in a suitable solvent or a mixture of solvents;
  iii) heating the composition to at least 60° C. and optionally carrying out a filtration to obtain a clear solution;
  iv) crystallizing and cooling the mixture to a temperature between 1° C. and 30° C., optionally adding more solvent or mixture of solvents; and
  v) isolating the obtained solid material and optionally drying the product.

23. The process of claim 22, characterized in that the molar ratio of 5-methyl-(6S)-tetrahydrofolic acid and the amino acid ethyl ester in step i) is in the range of from 1:1 to 1:3.

24. The process of claim 22, wherein the solvent is water.

25. The process of claim 22, wherein in step iii) and/or iv) seed crystals are added.

26. The process of claim 22, wherein the amino acid ethyl ester is L-phenylalanine ethyl ester or L-methionine ethyl ester.

27. The process of claim 26, wherein L-phenylalanine ethyl ester or L-methionine ethyl ester is added as a hydrochloride.

28. A pharmaceutical composition, food additive and/or preparation comprising the crystalline salt comprising 5-methyl-(6S)-tetrahydrofolic acid and an amino acid ethyl ester selected according to claim 1 and optionally one or more acceptable excipients.

29. The pharmaceutical composition according to claim 28 in the form of tablets, capsules, oral liquid preparations, powders, lyophilisates, granules, lozenges, reconstitutable powders, injectable or infusable solutions or suspensions or suppositories.

30. The pharmaceutical composition according to claim 28 further comprising at least one additional therapeutic agent.

31. The pharmaceutical composition according to claim 28, which is a pharmaceutical composition for oral, parenteral, intramuscular, intraspinal, intrathecal, peridontal, topical or rectal administration.

32. The pharmaceutical composition according to claim 28, wherein the amino acid ethyl ester is L-phenylalanine ethyl ester or L-methionine ethyl ester.

33. A method for producing a drug or a food comprising incorporating a crystalline salt comprising 5-methyl-(6S)-tetrahydrofolic acid and an amino acid ethyl ester according to claim 1 in the drug or food.

34. The method according to claim 33, wherein the amino acid ethyl ester is L-phenylalanine ethyl ester or L-methionine ethyl ester.

35. A method comprising administering a crystalline salt comprising 5-methyl-(6S)-tetrahydrofolic acid and an amino acid ethyl ester according to claim 1 in a treatment for homocysteine-lowering, or for a treatment of anemia, neural tube defects, cardiovascular diseases, depression, cognitive impairment, Alzheimer's disease and osteoporosis and/or dietary management of low plasma and/or low red blood cell and/or low cerebrospinal fluid and/or low peripheral or central nervous system folate.

36. The method according to claim 35, wherein the amino acid ethyl ester is L-phenylalanine ethyl ester or L-methionine ethyl ester.

37. The crystalline salt of claim 1 having at least 99 wt % or more chemical and/or stereoisomerical purity.

* * * * *